United States Patent [19]

Hagiwara et al.

[11] Patent Number: 5,116,531
[45] Date of Patent: May 26, 1992

[54] LIQUID CRYSTAL COMPOUND

[75] Inventors: Takashi Hagiwara; Noriko Yamakawa; Ichiro Kawamura, all of Tokyo, Japan

[73] Assignee: Showa Shell Sekiyu K.K., Tokyo, Japan

[21] Appl. No.: 573,751

[22] Filed: Aug. 28, 1990

[30] Foreign Application Priority Data

Aug. 28, 1989 [JP] Japan ................... 1-220659

[51] Int. Cl.$^5$ .................. C09K 19/12; C07C 69/76
[52] U.S. Cl. ................. 252/299.65; 252/299.01; 252/299.64; 560/59; 560/102
[58] Field of Search ........... 252/299.01, 299.6, 299.61, 252/299.65, 299.66, 299.67; 350/350 S, 350 R; 560/59, 61, 73, 102, 106, 107, 108, 109

[56] References Cited

U.S. PATENT DOCUMENTS

| | | | |
|---|---|---|---|
| 4,009,934 | 3/1977 | Goodwin et al. | 350/160 |
| 4,576,732 | 3/1986 | Isogai et al. | 252/299.65 |
| 4,596,667 | 6/1986 | Inukai et al. | 252/299.65 |
| 4,714,323 | 12/1987 | Katagiri et al. | 350/350 S |
| 4,728,458 | 3/1988 | Higuchi et al. | 252/299.65 |
| 4,753,752 | 6/1988 | Raynes et al. | 252/299.65 |
| 4,931,208 | 6/1990 | Furukawa et al. | 252/299.61 |

OTHER PUBLICATIONS

Japanese Journal of Applied Physics, vol. 26, No. 11, pp. L1787–L1789.
Japanese Journal of Applied Physics; vol. 27, No. 5, May, 1988, pp. L729–L732.
Vol. 28, No. 1, Jan. 1989, pp. L119–L120.
Vol. 28, No. 7, Jul. 1989, pp. L1261–L1264.
Vol. 28, No. 7, Jul. 1989, pp. L1265–L1268.
Vol. 29, No. 1, Jan. 1990, pp. L103–L106.
Vol. 29, No. 1, Jan. 1990, pp. L107–L110.
Vol. 29, No. 1, Jan. 1990, pp. L110–L114.
Vol. 29, No. 1, Jan. 1990, pp. L131–L137.
Vol. 29, No. 2, Feb. 1990, pp. L329–L332.
Vol. 29, No. 2, Feb. 1990, pp. L333–L335.
Vol. 29, No. 2, Feb. 1990, pp. L336–L338.
JP-A-1-213390 and Derwent Abstract Thereof.

*Primary Examiner*—Robert L. Stoll
*Assistant Examiner*—Shean C. Wu
*Attorney, Agent, or Firm*—Sughrue, Mion, Zinn, Macpeak & Seas

[57] ABSTRACT

A liquid crystal compound represented by formula (I):

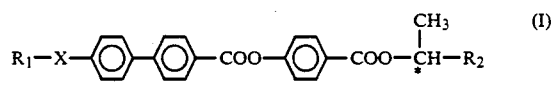

wherein $R_1$ represents an alkyl group having from 5 to 18 carbon atoms; $R_2$ represents an alkyl group having from 4 to 15 carbon atoms; X represents a single bond, —O—,

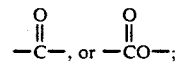

and * indicates an optically active center. The compound exhibits three stable states of molecular orientation.

3 Claims, 10 Drawing Sheets

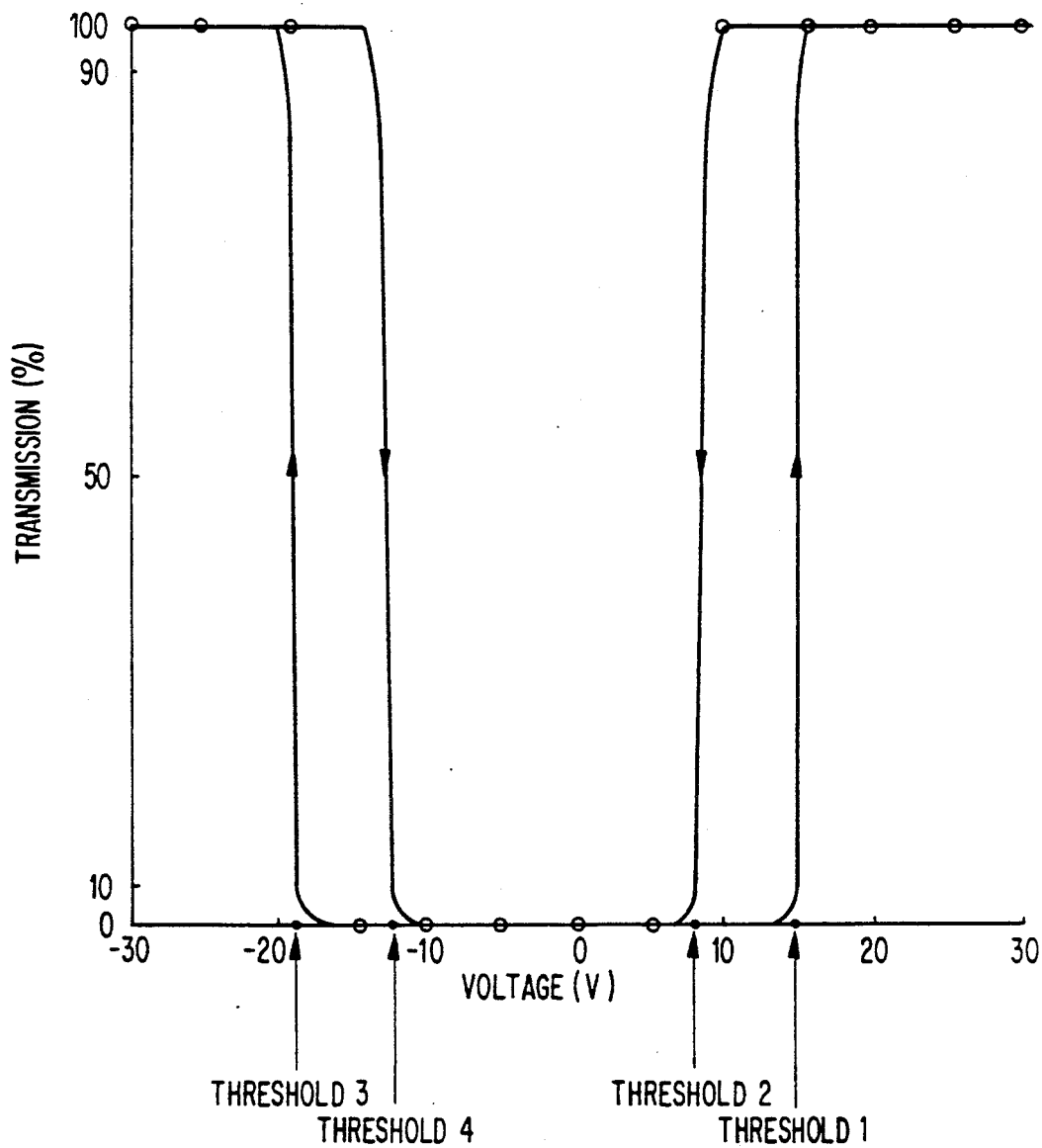

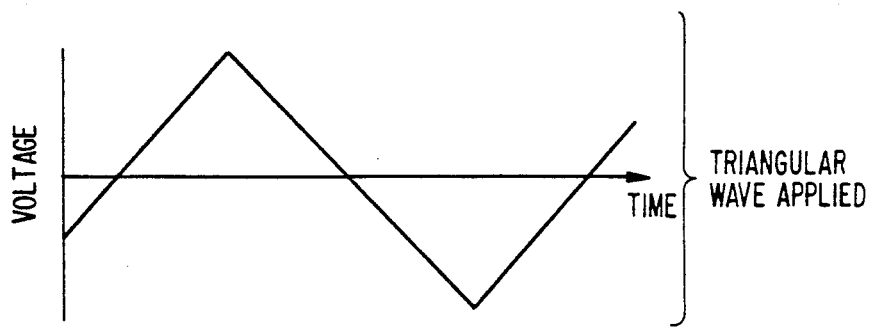
FIG. 4(A) TRIANGULAR WAVE APPLIED
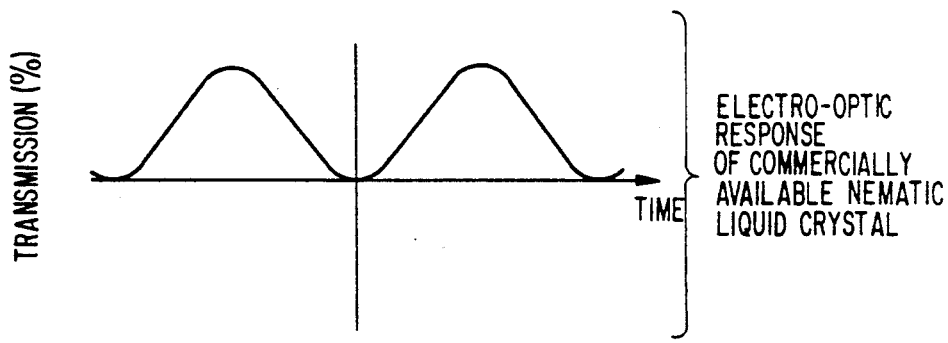
FIG. 4(B) ELECTRO-OPTIC RESPONSE OF COMMERCIALLY AVAILABLE NEMATIC LIQUID CRYSTAL
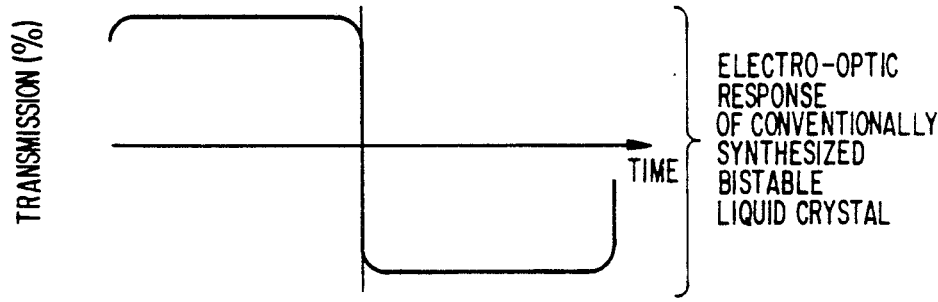
FIG. 4(C) ELECTRO-OPTIC RESPONSE OF CONVENTIONALLY SYNTHESIZED BISTABLE LIQUID CRYSTAL
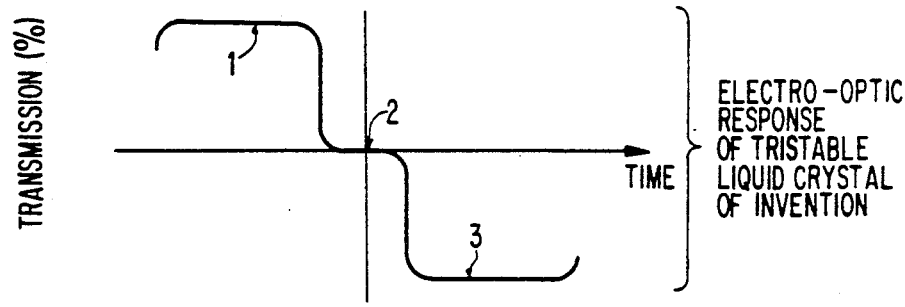
FIG. 4(D) ELECTRO-OPTIC RESPONSE OF TRISTABLE LIQUID CRYSTAL OF INVENTION

LIQUID CRYSTAL COMPOUND

FIELD OF THE INVENTION

This invention relates to a ferroelectric chiral smectic liquid crystal compound which is suitable for use in an electro-optic display device. This invention also relates to a ferroelectric liquid crystal compound exhibiting three stable molecular orientation states which is suitable for use in display elements or electro-optic elements utilizing a response to an electric field.

BACKGROUND OF THE INVENTION

Electro-optic devices using liquid crystals which have been developed and put into practical use to date include those using nematic liquid crystals, such as a DSM mode, a TN mode, a G-H mode, and an STN mode. However, such devices using nematic liquid crystals have a very slow electro-optic response and require a switching time from several to several ten milliseconds and are thus limited in their range of application. The slow response of these elements using nematic liquid crystals is due to the fact that the torque of moving molecules, which is basically based on the anisotropy of their dielectric constant, is not very high.

In light of the above, Meyer et al developed ferroelectric liquid crystals which undergo spontaneous polarization (Ps) which have a strong torque, the torque being based on Ps x E (the applied electric field), and which thus have a high speed response on the order of microseconds, as disclosed in Le Journal de Physique, Vol. 36, L-69 (1975). Further, JP-A No. 63-307837 (the term "JP-A" as used herein means an "unexamined published Japanese patent application") discloses new ferroelectric liquid crystals, but has no disclosure on the "three states" concept hereinafter discussed.

Several high speed electro-optic devices using ferroelectric liquid crystals have been proposed to date. Typically, such devices include an element in which a twisted structure is untwisted by the force of wall surfaces, and two molecular alignment layers in parallel to the wall surface are varied by changing the polarity of an applied electric field as described, e.g., in JP-A No. 56-107216.

The use of a compound showing ideal two states having an electric field response waveform as shown in FIG. 1 is a prerequisite in the above described devices. However, such a compound exhibiting ideal two (bistable) states is not yet available. The so far synthesized bistable liquid crystals have a response waveform as shown in FIG. 2, not as shown in FIG. 1. When the state-of-the-art liquid crystals having a response waveform as shown in FIG. 2 are used, for example, in light switching circuits, since transmission gradually changes as the applied voltage changes from negative to positive, the desired results cannot be sufficiently achieved simply by changing the applied voltage between "on" and "off". Moreover, currently available bistable liquid crystals have difficulty in reaching a mono-domain state in their Sc* phase without an applied voltage, i.e., in reaching an ideal molecular orientation state, and easily undergo the defect or a molecular orientation disturbance called twist. Thus, it has been difficult to achieve the above ideal two states of molecular orientation over a wide range.

Further, because the threshold value (voltage at which luminance changes by a prescribed value) is low, dynamic driving is liable to suffer from a reduction in contrast or a reduction in the viewing angle.

Further, these conventional bistable liquid crystals do not exhibit a hysteresis loop as shown in FIG. 1 but exhibit hysterisis as shown in FIG. 2 so they have no memory effect. Therefore, it is necessary to continue applying a voltage $v_3$ as shown in FIG. 2 or continue applying a high frequency for the liquid crystal to maintain a stable response in the Sc* phase, which, in either case, results in a considerable energy loss.

Thus, conventional electro-optic devices have many defects which need to be overcome, notwithstanding the strong demand for devices which make effective use of the characteristics of electro-optic devices to use an applied electric field to achieve molecular orientation of ferroelectric liquid crystals.

SUMMARY OF THE INVENTION

An objective of this invention is to provide a novel liquid crystal compound which exhibits a stable molecular orientation state having a high light/shade contrast in the lack of an applied electric field, which has well defined threshold characteristics and a well defined hysteresis curve or loop as shown in FIG. 3, which easily undergoes dynamic driving, and which can be used in liquid crystal electro-optic devices involving three states, which make it possible to obtain a high-speed response.

More specifically, an objective of this invention is to provide a novel ferroelectric chiral smectic liquid crystal compound exhibiting three molecular orientation states which is entirely different from a chiral smectic C phase (Sc* phase) which is a conventional bistable state phase.

The terminology "three states" as used herein means three stable molecular orientation states as now explained. In a liquid crystal electro-optic device comprising a pair of electrode substrates with a prescribed gap therebetween and a ferroelectric liquid crystal sandwiched between the pair of substrates, the electrodes are connected to an electric power source so that voltage of a triangular waveform as shown in FIG. 4(A) is applied thereto. The ferroelectric liquid crystal shows a first stable molecular orientation state as shown by numeral 2 in FIG. 4(D) when no electric field is applied thereto, a second stable molecular orientation state as shown by numeral 1 in FIG. 4(D) differing from the first stable state when an electric field is applied to one direction, and a third stable molecular orientation state as shown by numeral 3 of FIG. 4(D) differing from either of the first and second stable states when an electric field is applied to another direction. With respect to liquid crystal electro-optic devices utilizing these three stable states, the inventors have already filed Japanese patent application No. Sho-63-70212.

On the contrary, commercially available nematic liquid crystals synthesized to date are bistable liquid crystals which do not have such three stable states, as shown in FIGS. 4(B) and (C), respectively.

The above ferroelectric liquid crystals having three states (hereinafter sometimes referred to as tristable liquid crystals) according to the present invention produce striking effects when applied to liquid crystal displays as compared with conventional nematic liquid crystals as now discussed.

While conventional liquid crystals must be driven using a very complicated system called an active matrix system, the tristable ferroelectric liquid crystals of the present invention can be driven using a simple matrix display. Accordingly, a display element using the tristable ferroelectric liquid crystal can be produced in a simple manner, which makes it feasible to widen the display area and to reduce production costs, whereas conventional display elements require complicated production steps, encounter difficulty in widening the display area, and involve high production costs.

The present invention provides a liquid crystal compound represented by formula (I):

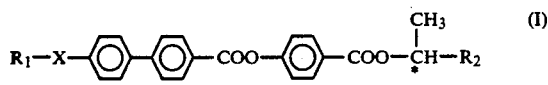

wherein $R_1$ represents an alkyl group having from 5 to 18 carbon atoms; $R_2$ represents an alkyl group having from 4 to 15 carbon atoms; X represents a single bond, —O—,

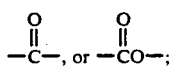

and * indicates an optically active center, which exhibits three stable states consisting of these structures.

BRIEF DESCRIPTION OF THE DRAWINGS

FIGS. 1, 2, and 3 each show the hysteresis curve or loop of an ideal bistable liquid crystal (which is not actually available), of a conventional bistable liquid crystal, and a tristable liquid crystal according to the present invention, respectively, in which the applied voltage is plotted as the abscissa and the transmission (%) as the ordinate.

FIG. 4(A) shows the triangular wave applied.

FIGS. 4(B), (C), and (D) each show the electrooptic response of a commercially available nematic liquid crystal, a conventionally synthesized bistable liquid crystal, and a tristable liquid crystal according to the present invention, respectively, when the triangular wave of FIG. 4(A) is applied.

DETAILED DESCRIPTION OF THE INVENTION

Figure 1:
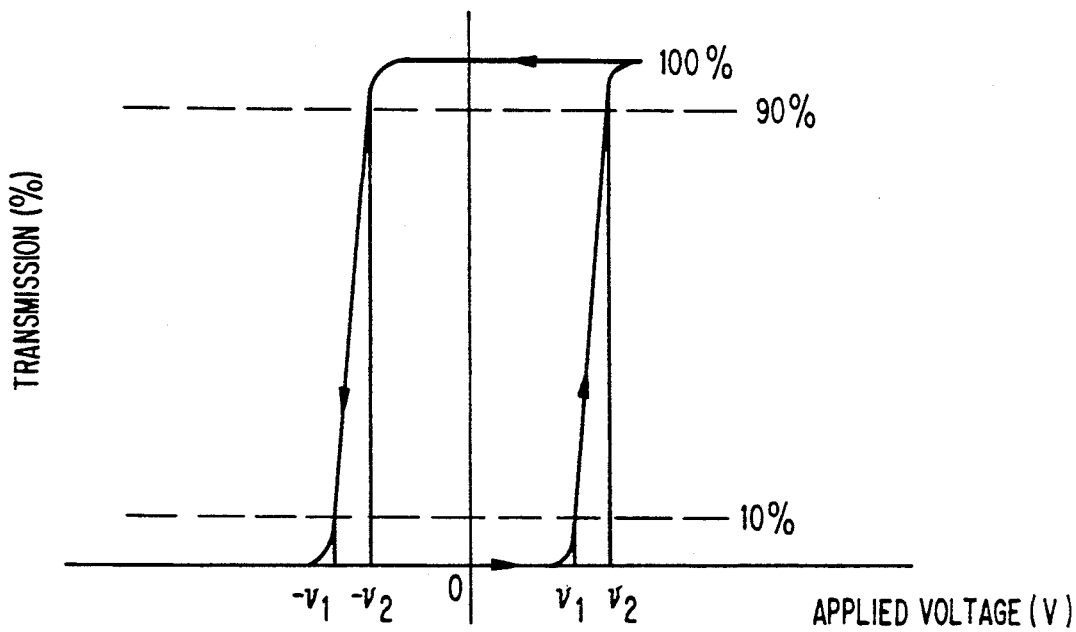
Figure 2:
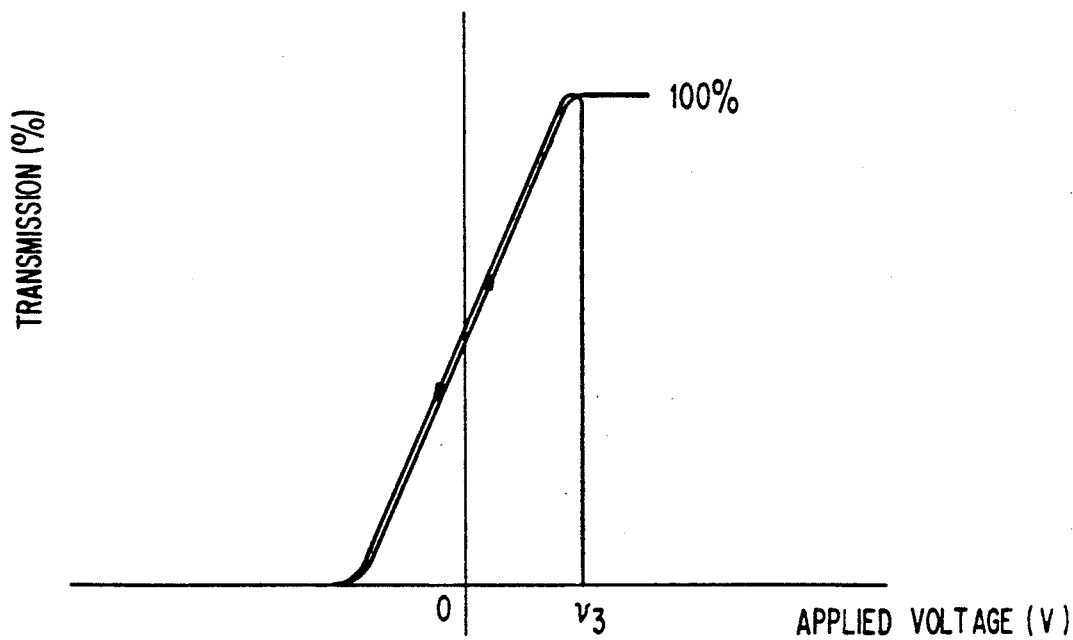

Specific examples of preferred compounds represented by formula (I) are shown below.

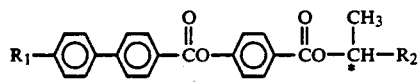

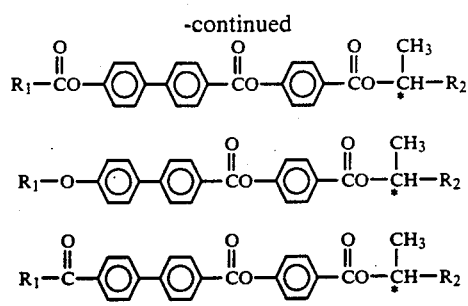

wherein $R_1$ and $R_2$ are as earlier defined.

In the above formulae, $R_1$ preferably represents a straight chain alkyl group having from 6 to 12 carbon atoms; and $R_2$ preferably represents a straight chain alkyl group having from 5 to 12 carbon atoms.

The compounds according to the present invention can be synthesized with reference to JP-A Nos. 60-32747, 61-210056 and 62-48651.

Generally, mild reaction conditions are used for the synthesis of desired compounds. Synthesis is carried out at room temperature for 12 hours under atmospheric pressure.

Specifically, the compounds according to the present invention can be synthesized by, for example, a process comprising reacting a 4-benzyloxybenzoic acid derivative and an optically active 2-alkanol to obtain a 4-benzyloxybenzoic acid-1-methyl alkyl ester, followed by reduction to obtain 4-hydroxybenzoic acid-1-methyl alkyl ester. Such ester was reacted with a 4'-alkanoyloxybiphenyl-4-carboxylic acid in the presence of dicyclohexylcarbodiimide (DCC) to obtain a 1-methylalkyl 4'-alkanoyloxybiphenyl-4-carboxylate.

The present invention is now illustrated in greater detail by way of Examples, but it should be understood that the present invention is not deemed to be limited thereto. In the Examples, the phase transition temperatures of the liquid crystals obtained were measured by microscopic observation using temperature controlled hot stage in which a liquid crystal cell was placed.

EXAMPLE 1

(1) Synthesis of 1-Methylheptyl 4-Benzyloxybenzoate

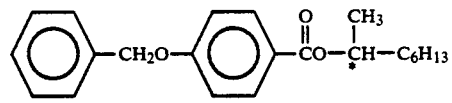

In 10 ml of methylene chloride was dissolved 1.23 g of 4-benzyloxybenzoic acid chloride, and a solution of 0.59 g of optically active 2-octanol, 0.55 g of dimethylaminopyridine, and 0.48 g of triethylamine in 20 ml of methylene chloride was added thereto in small portions under ice cooling.

The reaction mixture was allowed to warm to room temperature and was allowed to react at that temperature for one day. The reaction mixture was poured into ice water and extracted with methylene chloride. The methylene chloride phase was washed successively with diluted hydrochloric acid, water, an aqueous 1N sodium carbonate solution, and water and dried over anhydrous magnesium sulfate. The solvent was removed by distillation to obtain a crude product. The crude product was purified by column chromatography using silica gel and toluene and then recrystallized from ethanol to obtain 1.48 g of the titled compound.

(2) Synthesis of 1-Methylheptyl 4-Hydroxybenzoate

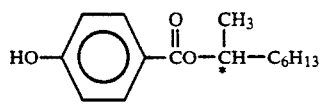

The compound obtained in (1) above was dissolved in 15 ml of ethanol, and 0.36 g of 10 % palladium-on-carbon was added to the solution to conduct hydrogenation in a hydrogen atmosphere to obtain 1.29 g of the titled compound.

(3) Synthesis of 4-(1-Methylheptyloxycarbonyl)phenyl 4'-n-Nonanoyloxybiphenyl-4-carboxylate

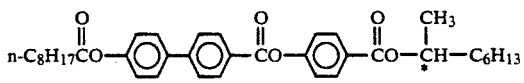

In 330 ml of dehydrated tetrahydrofuran were dissolved 5.00 g of 4'-nonanoyloxybiphenyl-4-carboxylic acid and 6.76 g of 1-methylheptyl 4-hydroxybenzoate synthesized in (2) above. To the solution were added 6.18 g of DCC and 0.24 g of dimethylaminopyridine, followed by stirring for one day at room temperature.

The reaction mixture was then filtered, and tetrahydrofuran was removed from the filtrate by distillation. The residue was dissolved in methylene chloride and washed with a small amount of water. The collected methylene chloride layer was dehydrated over anhydrous magnesium sulfate. Methylene chloride was then removed by distillation, and the resulting crude product was purified by column chromatography using silica gel and then recrystallized from ethanol to obtain 2.83 g of the desired optically active compound.
$[\alpha]_D^{25} = -20.9°$
Phase Transition Temperatures (°C.):

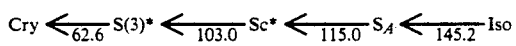

Figure 6:
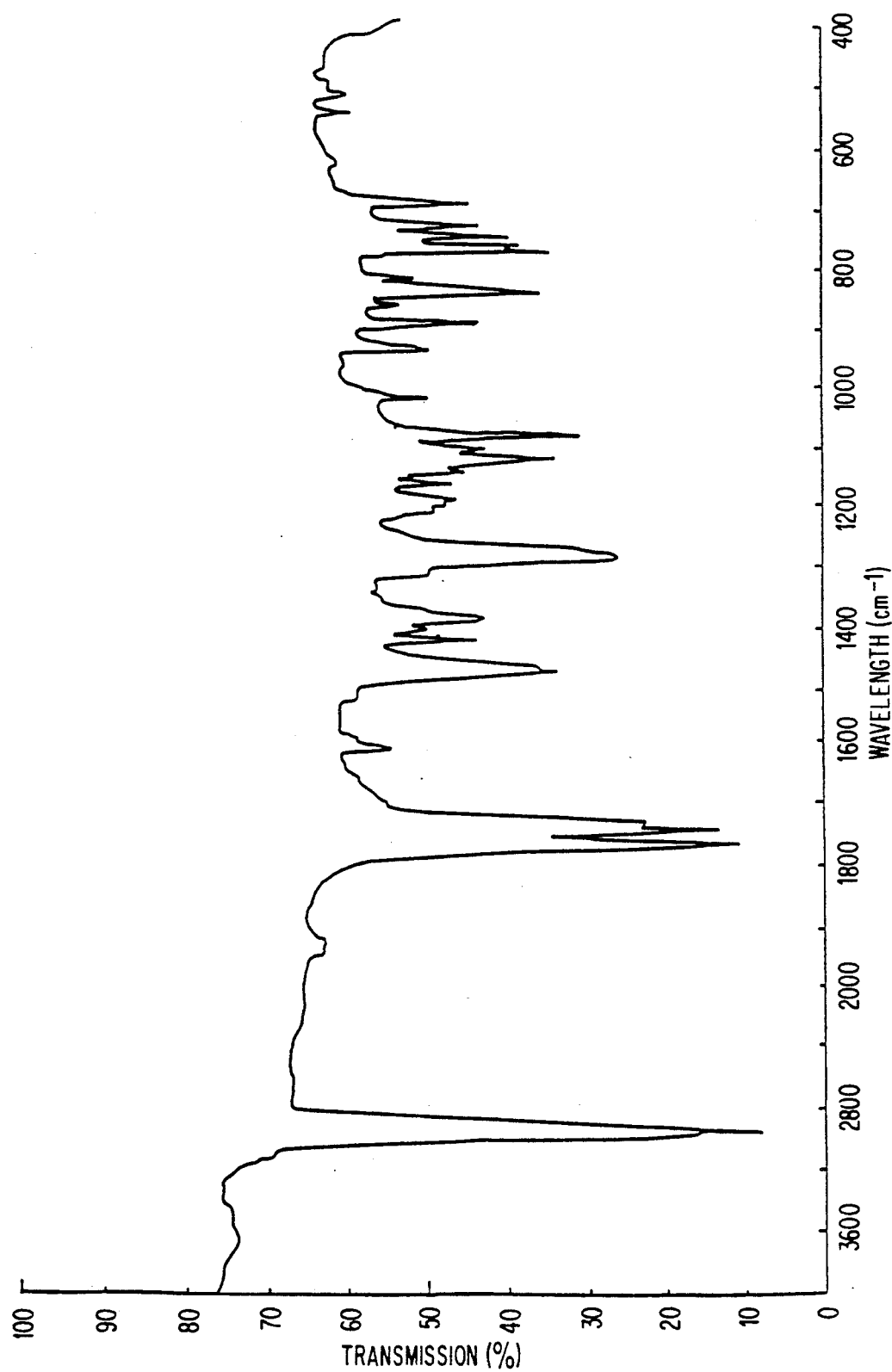
FIGS. 6 through 9 each show the infrared absorption spectrum of the compounds prepared in Examples 1 to 4.

The infrared absorption spectrum (KBr) of the compound is shown in FIG. 6.

EXAMPLE 2

Synthesis of 4-(1-Methylheptyloxycarbonyl)-phenyl 4'-n-Octylbiphenyl-4-carboxylate

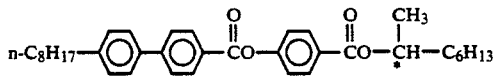

The titled optically active compound was synthesized in the same manner as in Example 1, except for replacing 4'-nonanoyloxybiphenyl-4-carboxylic acid as used in Example 1-(3) with 4'-octylbiphenyl-4-carboxylic acid.
$[\alpha]_D^{25} = -22.3°$
Phase Transition Temperatures (°C.)

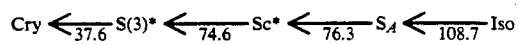

Figure 7:
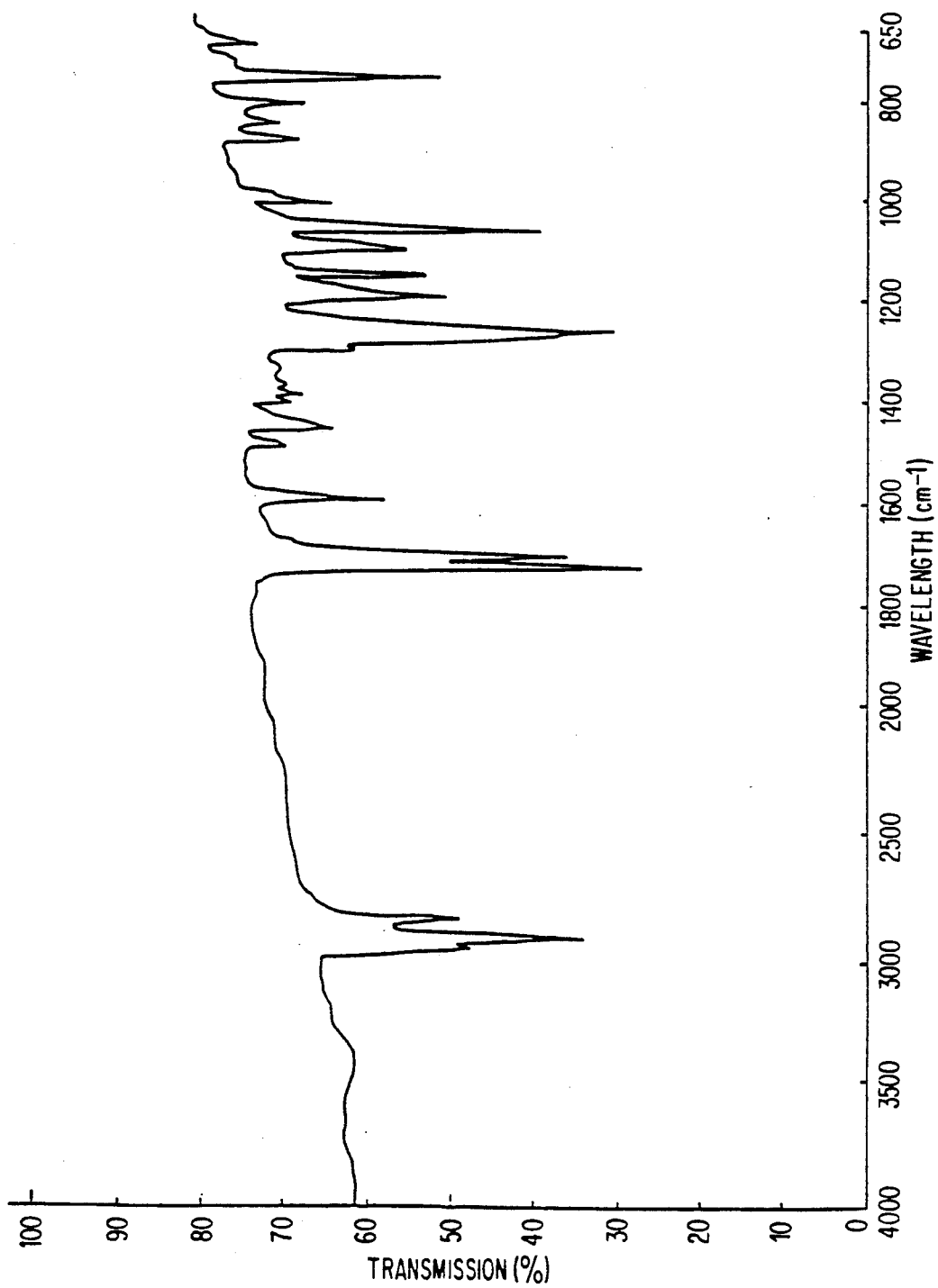

The infrared absorption spectrum (KBr) of the compound is shown in FIG. 7.

EXAMPLE 3

Synthesis of 4-(1-Methylheptyloxycarbonyl) phenyl 4'-n-Octyloxybiphenyl-4-carboxylate The titled optically active compound was synthesized in the same manner as in Example 1, except for replacing 4'-nonanoyloxybiphenyl-4-carboxylic acid as used in Example 1-(3) with 4'-octyloxybiphenyl-4-carboxylic acid.
$[\alpha]_D^{25} = -22.5°$
Phase Transition Temperatures (°C.):

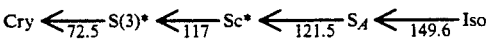

Figure 8:
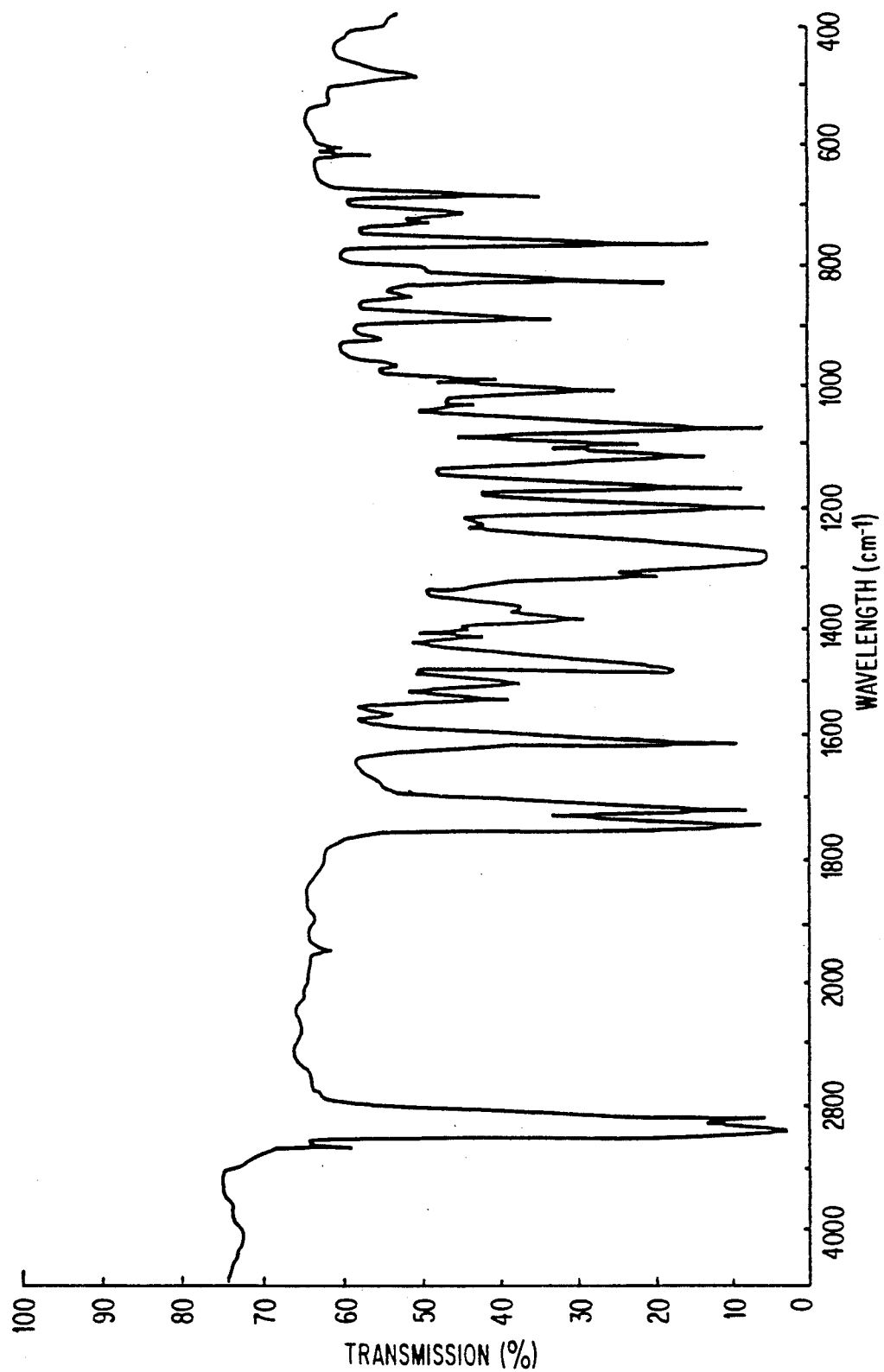

The infrared absorption spectrum (KBr) of the compound is shown in FIG. 8.

EXAMPLE 4

Synthesis of 4-(1-Methylheptyloxycarbonyl) phenyl 4'-n-Nonanoylbiphenyl-4-carboxylate

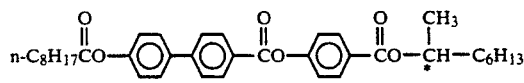

The titled compound was obtained in the same manner as in Example 1, except for replacing 4'-nonanoyloxybiphenyl-4-carboxylic acid as used in Example 1-(3) with 4'-nonanoylbiphenyl-4-carboxylic acid.
$[\alpha]_D^{25} = -21.2°$
Phase Transition Temperatures (°C.):

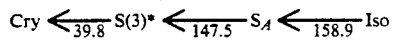

Figure 9:
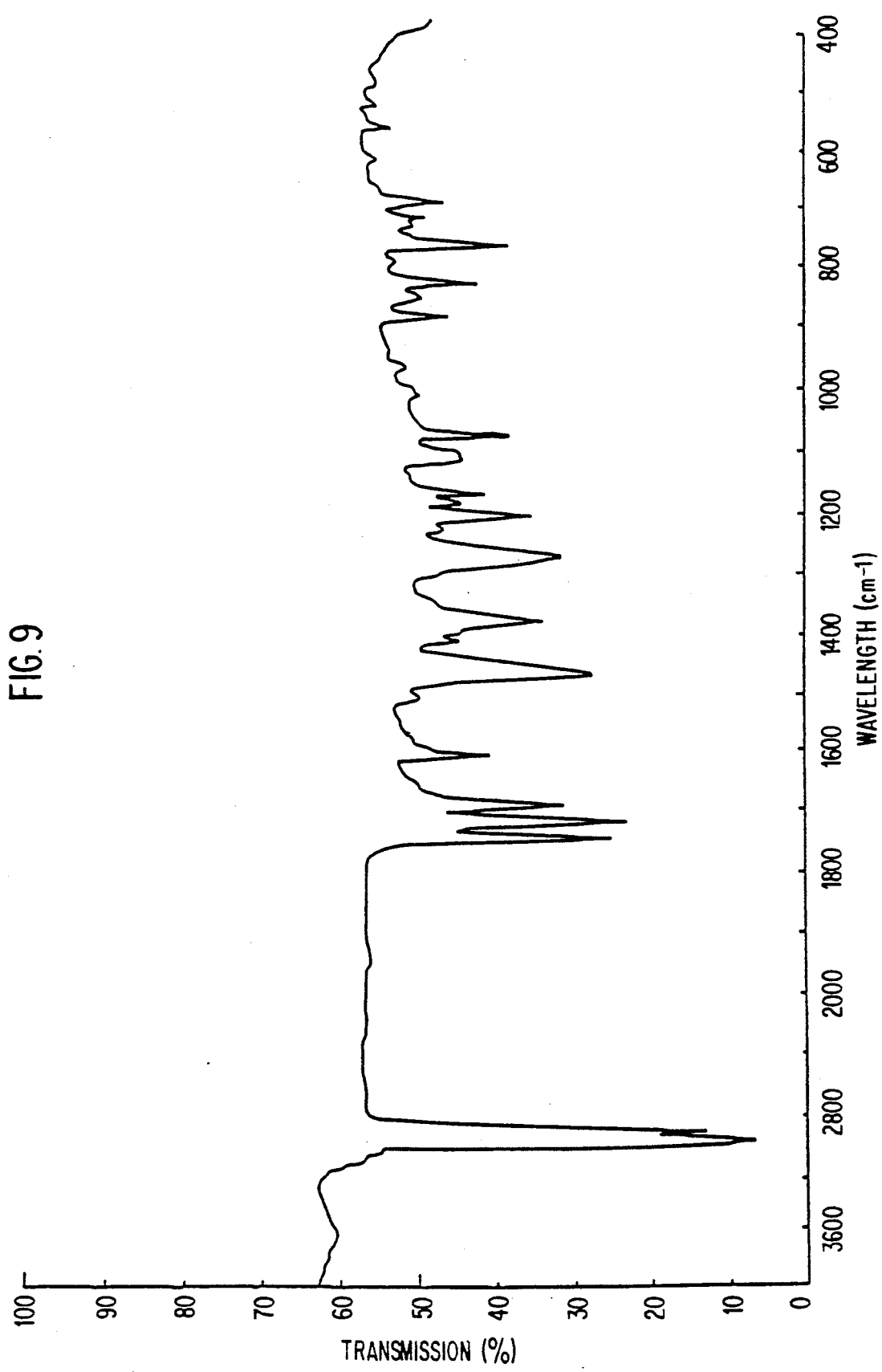

The infrared absorption spectrum (KBr) of the compound is shown in FIG. 9.

EXAMPLE 5

The liquid crystal compound obtained in Example 1 was filled, while in an isotropic phase, into a liquid crystal cell having a polyimide orientation film which had been subjected to a rubbing treatment on an ITO (indium tin oxide) electrode substrate (cell thickness: 2.9 μm).

Figure 10:
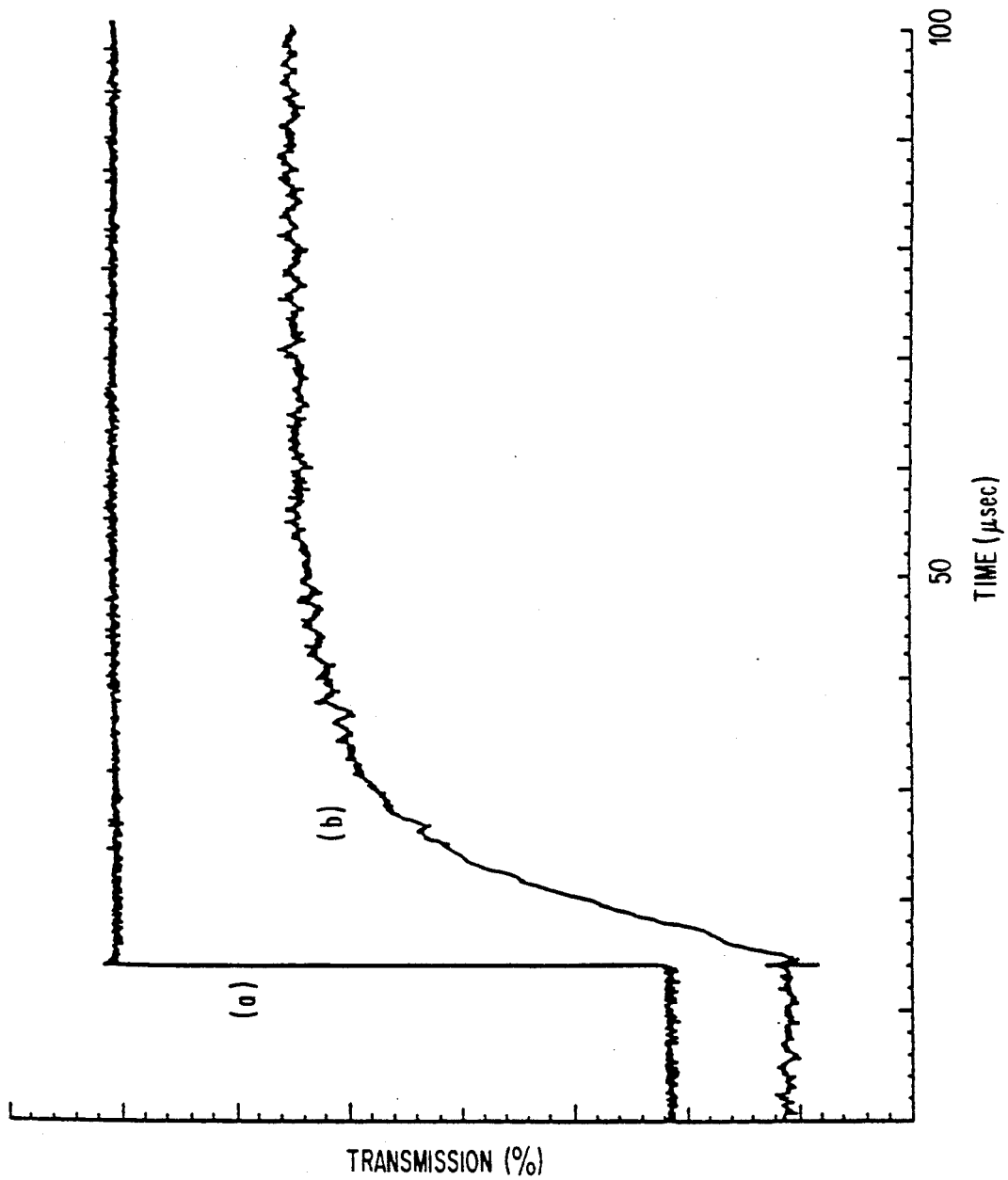
FIG. 10 shows the electro-clinic effect, in which (a) is an alternating voltage applied to a liquid crystal electrooptic element, and (b) shows the changes of transmission with alternating voltage (a).

The resulting cell was slowly cooled at a cooling rate of 0.1 to 1.0 °C./min to orientate the liquid crystal molecules in an SA phase. A square wave voltage of ±30 V and 10 Hz was applied, and the electro-optic response was detected with a polarizing microscope equipped with a photomultiplier. As a result, an electro-clinic effect (b) optically responding to the applied electric field (a) was observed in the $S_A$ phase as shown in FIG. 10. The same effect was observed in liquid crystal cells Obtained by using other liquid crystal compounds prepared in the foregoing Examples.

EXAMPLE 6

Figure 5:
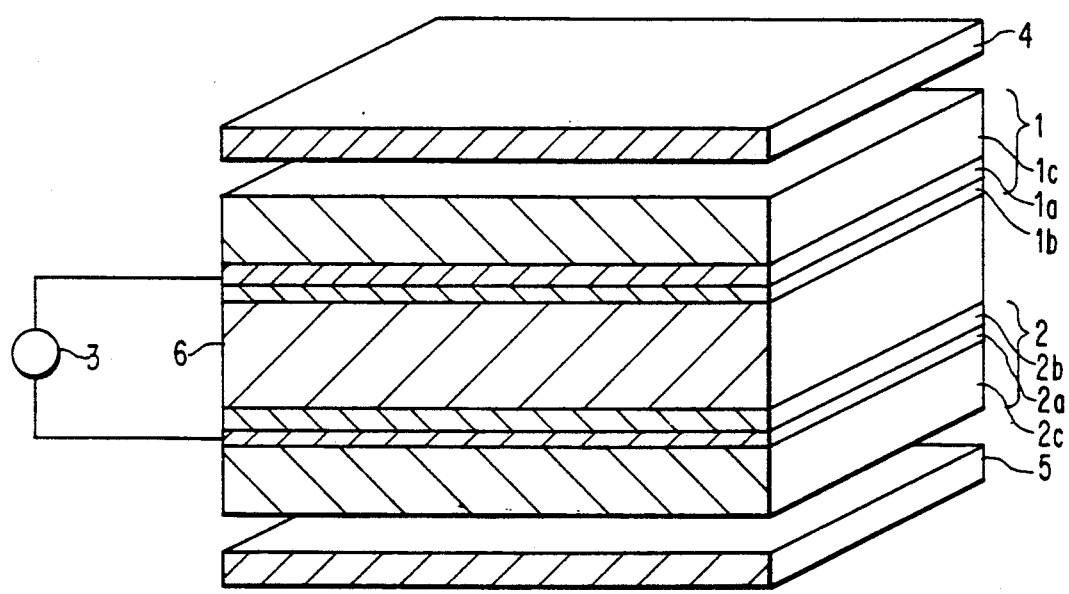
FIG. 5 illustrates a structure of the liquid crystal element according to the present invention.
Figure 11:
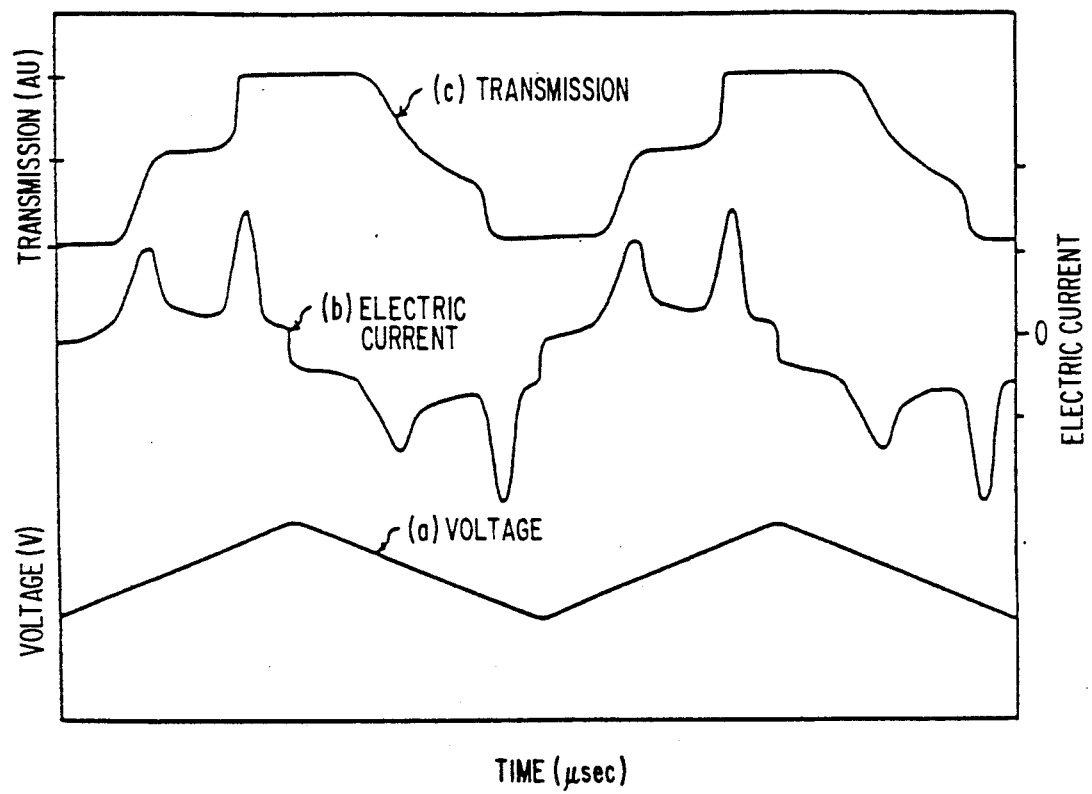
FIG. 11 illustrates switching among the three states of a compound according to the present invention, in which (a) is the triangular voltage wave applied to the liquid crystal electro-optic element, (b) is the polarization inversion current; and (c) is the transmission change with the voltage (a).

The liquid crystal cell as shown in FIG. 5 prepared in the same manner as in Example 5 was set in a polarizing microscope equipped with a photomultiplier having a pair of crossing polarizing sheets in such a manner that the direction of the molecular longer axis with −30 voltage applied and the polarizer was in parallel. Then, the cell was gradually cooled at a cooling rate of 0.1 to 1.0 °C./min until it exhibited an S(3)* phase. The cell was further cooled and in the temperature range of from 103.0° C. to 62.2° C., a triangular wave voltage (a) of ±30 V and 10 Hz was applied thereto. As shown in FIG. 11, the transmission (c) changed into three states, i.e., a shade state with a minus voltage applied, an intermediate state with a voltage of zero, and a light state with a plus voltage applied.

There is illustrated a structure of a liquid crystal electro-optic cell in FIG. 5, in which 1 and 2 each represents an electrode substrate which is composed of a transparent electrode (1a, 2a), an orientation control film (1b, 2b) and a transparent substrate (1c, 2c), 3 represents an external electrical source, 4 and 5 represents a polarizer, and 6 represents a ferroelectric liquid crystal.

Two electrode substrates arranged to be parallel to each other and spaced by 2.9 micrometers using sealant. Electrodes constructed by a transparent conductive film made of an indium tin oxide, on the inner surfaces of the transparent electrodes. An orientation polyimide film was coated on the conductive electrode surfaces. In addition it is also appropriate to apply, for the orientation of the liquid crystals generally known rubbing process to the polyimide coated electrode substrates.

The electrode substrates are combined to be parallel to each other so that the liquid crystal is arranged in one direction. Thereafter, the ferroelectric liquid crystal materials shown by the formulas described already is heated so as to become an isotropic phase which in turn slowly cooled in units of 0.1° to 1.0° C. per minute up to the chiral smectic C phase.

The liquid crystal cell prepared in this manner was set in a polarizing microscope equipped with a photomultiplier having a pair of cross nichol polarizer in such a manner that the direction of the molecular layer axis with −30 voltage applied and the polarizer was in parallel. Then the cell was gradually cooled at a cooling rate of 0.1° to 1.0° C./min unit it exhibited a S(3)* phase.

The cell was further cooled, and in the temperature range of from 103.0° C. to 62.6° C., a triangular wave voltage (a) of ±30 V and 10 Hz was applied thereto. As shown in FIG. 11, the transmission (C) changed into three states i.e., a shade state with a minus voltage applied, an intermediate state with a voltage of 3000, and a light state with a plus voltage applied.

The polarization inversion current waveform (b) also showed peaks corresponding to these changes, i.e., the liquid crystal molecules proved to exhibit three stable states of molecular orientation. A similar effect was observed in liquid crystal cells using other liquid crystal compounds obtained in the foregoing Examples.

As described above, the novel liquid crystal compounds of the present invention exhibit three stable states and can be utilized in a wide range of applications, such as in display devices and switching devices.

While the invention has been described in detail and with reference to specific embodiments thereof, it will be apparent to one skilled in the art that various changes and modifications can be made therein without departing from the spirit and scope thereof.

What is claimed is:

1. A liquid crystal compound represented by formula (I):

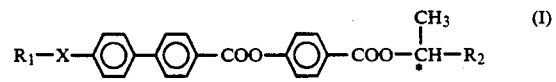

wherein $R_1$ represents a straight chain alkyl group having from 5 to 18 carbon atoms; $R_2$ represents a straight chain alkyl group having from 4 to 15 carbon atoms; X represents

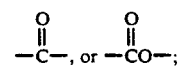

and indicates an optically active center, which exhibits three stable states.

2. A liquid crystal compound as claimed in claim 1, wherein $R_1$ represents a straight chain alkyl group having from 6 to 12 carbon atoms; and $R_2$ represents a straight chain alkyl group having from 5 to 12 carbon atoms.

3. A liquid crystal compound as claimed in claim 1, which is in the S*(3) phase, and which has three stable states.

* * * * *